United States Patent
Whalen et al.

(10) Patent No.: US 7,048,698 B2
(45) Date of Patent: May 23, 2006

(54) URETHRAL PROFILING DEVICE AND METHODOLOGY

(75) Inventors: Mark J. Whalen, Alexandria, MN (US); Lloyd K. Willard, Miltona, MN (US); John M. Reid, Garfield, MN (US)

(73) Assignee: AbbeyMoor Medical, Inc., Miltona, MN (US)

( * ) Notice: Subject to any disclaimer, the term of this patent is extended or adjusted under 35 U.S.C. 154(b) by 329 days.

(21) Appl. No.: 10/179,108

(22) Filed: Jun. 24, 2002

(65) Prior Publication Data

US 2002/0198506 A1 Dec. 26, 2002

Related U.S. Application Data

(60) Provisional application No. 60/299,973, filed on Jun. 22, 2001, and provisional application No. 60/324,366, filed on Sep. 24, 2001.

(51) Int. Cl.
*A61B 51/03* (2006.01)

(52) U.S. Cl. ............................ 600/587; 33/512
(58) Field of Classification Search ................ 600/587, 600/591, 29, 38, 31; 604/544, 264, 96.01; 33/511, 512
See application file for complete search history.

(56) References Cited

U.S. PATENT DOCUMENTS

| | | | |
|---|---|---|---|
| 2,078,686 A | 4/1937 | Rowe | |
| 2,450,217 A | 9/1948 | Alcorn | |
| 2,687,131 A | 8/1954 | Raiche | |
| 3,136,316 A | 6/1964 | Beall | |
| 3,495,620 A | 2/1970 | Raimondi et al. | |
| 3,630,206 A | 12/1971 | Gingold | |
| 3,642,004 A | 2/1972 | Osthagen et al. | |
| 3,706,307 A | * 12/1972 | Hasson | 600/591 |
| 3,731,670 A | 5/1973 | Loe | |
| 3,742,960 A | 7/1973 | Dye et al. | |
| 3,812,841 A | 5/1974 | Isaacson | |
| 3,908,637 A | 9/1975 | Doroshow | |
| 4,121,572 A | 10/1978 | Krzeminski | |
| 4,217,911 A | 8/1980 | Layton | |
| 4,249,536 A | 2/1981 | Vega | |
| 4,301,811 A | 11/1981 | Layton | |
| 4,407,301 A | 10/1983 | Streisinger | |
| 4,432,757 A | 2/1984 | Davis, Jr. | |
| 4,484,585 A | 11/1984 | Baier | |
| 4,489,732 A | * 12/1984 | Hasson | 600/591 |
| 4,500,313 A | * 2/1985 | Young | 604/544 |
| 4,501,580 A | 2/1985 | Glassman | |

(Continued)

FOREIGN PATENT DOCUMENTS

WO  WO 00/21462  4/2000

OTHER PUBLICATIONS

Vicente, J. et al. *Spiral Urethral Prosthesis as an Alternative to Surgery in High Risk Patients with Benign Prostatic Hyperplasia: Prospective Study*. The Journal of Urology. vol. 142. p. 1504. Copyright 1989.
Fabian, K. M. *Der interprostatische "partielle Katheter"*. Urologe. vol. 23. pp. 229–233. 1984.
Fabian, K. M. *Der Intraprostatische "Partielle Katheter"*. Urologe. 1980.

*Primary Examiner*—Charles Marmor
(74) *Attorney, Agent, or Firm*—Nawrocki, Rooney & Sivertson, P.A.

(57) ABSTRACT

A urethral profile apparatus, assembly and appurtenant methodology is provided. The apparatus includes an elongate member having proximal and distal ends, the proximal end including a probe. The probe is selectively positionable within a urethral passageway by axial translation of the elongate member via the distal end, with the probe dimensioned so as to indicate constrictures of the urethral passageway.

19 Claims, 26 Drawing Sheets

U.S. PATENT DOCUMENTS

| | | |
|---|---|---|
| 4,538,621 A | 9/1985 | Jarczyn |
| 4,553,533 A | 11/1985 | Leighton |
| 4,553,959 A | 11/1985 | Hickey et al. |
| 4,612,939 A | 9/1986 | Robertson |
| 4,721,095 A | 1/1988 | Rey et al. |
| 4,737,147 A | 4/1988 | Ferrando et al. |
| 4,781,677 A | 11/1988 | Wilcox |
| 4,792,335 A | 12/1988 | Goosen et al. |
| 4,865,030 A | 9/1989 | Polyak |
| 4,865,588 A | 9/1989 | Flinchbaugh |
| 4,873,990 A | 10/1989 | Holmes et al. |
| 4,909,785 A | 3/1990 | Burton et al. |
| 4,932,938 A | 6/1990 | Goldberg et al. |
| 4,932,958 A | 6/1990 | Reddy et al. |
| 4,934,999 A | 6/1990 | Bader |
| 4,946,449 A | 8/1990 | Davis, Jr. |
| 5,030,199 A | 7/1991 | Barwick et al. |
| 5,041,092 A | 8/1991 | Barwick |
| 5,059,169 A | 10/1991 | Zilber |
| 5,071,429 A | 12/1991 | Pinchuk et al. |
| 5,088,980 A | 2/1992 | Leighton |
| 5,090,424 A | 2/1992 | Simon et al. |
| 5,112,306 A | 5/1992 | Burton et al. |
| 5,114,398 A | 5/1992 | Trick et al. |
| 5,140,999 A | 8/1992 | Ardito |
| 5,234,409 A | 8/1993 | Goldberg et al. |
| 5,242,398 A * | 9/1993 | Knoll et al. ........... 604/103.05 |
| 5,250,029 A | 10/1993 | Lin et al. |
| 5,254,089 A | 10/1993 | Wang |
| 5,271,735 A | 12/1993 | Greenfeld et al. |
| 5,295,979 A | 3/1994 | DeLaurentis et al. |
| 5,320,605 A | 6/1994 | Sahota |
| 5,322,501 A | 6/1994 | Mahmud-Durrani |
| 5,360,402 A | 11/1994 | Conway et al. |
| 5,366,506 A | 11/1994 | Davis |
| 5,380,268 A | 1/1995 | Wheeler |
| 5,385,563 A | 1/1995 | Gross |
| 5,403,280 A | 4/1995 | Wang |
| 5,427,115 A | 6/1995 | Rowland et al. |
| 5,429,620 A | 7/1995 | Davis |
| 5,437,604 A | 8/1995 | Kulisz et al. |
| 5,483,976 A | 1/1996 | McLaughlin et al. |
| 5,512,032 A | 4/1996 | Kulisz et al. |
| 5,527,336 A | 6/1996 | Rosenbluth et al. |
| 5,609,583 A | 3/1997 | Hakki et al. |
| 5,657,764 A | 8/1997 | Coulter et al. |
| 5,711,314 A | 1/1998 | Ardito |
| 5,713,877 A | 2/1998 | Davis |
| 5,718,686 A | 2/1998 | Davis |
| 5,724,994 A | 3/1998 | Simon et al. |
| 5,735,831 A | 4/1998 | Johnson et al. |
| 5,752,525 A | 5/1998 | Simon et al. |
| 5,762,599 A | 6/1998 | Sohn |
| 5,766,209 A | 6/1998 | Devonec |
| RE35,849 E | 7/1998 | Soehendra |
| 5,776,081 A | 7/1998 | Kreder |
| 5,785,641 A * | 7/1998 | Davis .......................... 600/30 |
| 5,813,974 A | 9/1998 | Guardia |
| 5,864,961 A | 2/1999 | Vaughan |
| 5,876,417 A | 3/1999 | Devonec et al. |
| 5,916,195 A | 6/1999 | Eshel et al. |
| 5,964,732 A | 10/1999 | Willard |
| 5,971,967 A | 10/1999 | Willard |
| 5,976,068 A | 11/1999 | Hakky et al. |
| 6,004,290 A | 12/1999 | Davis |
| 6,022,312 A | 2/2000 | Chaussy et al. |
| 6,033,413 A | 3/2000 | Mikus et al. |
| 6,056,699 A | 5/2000 | Sohn et al. |
| 6,083,179 A | 7/2000 | Oredsson |
| 6,105,580 A | 8/2000 | Von Iderstein et al. |
| 6,132,365 A | 10/2000 | Sigurdsson |
| 6,167,886 B1 | 1/2001 | Engel et al. |
| 6,221,060 B1 | 4/2001 | Willard |
| 6,234,956 B1 | 5/2001 | He et al. |
| 6,447,462 B1 | 9/2002 | Wallace et al. |
| 6,494,848 B1 * | 12/2002 | Sommercorn et al. ...... 600/587 |
| 6,494,879 B1 | 12/2002 | Lennox et al. |

* cited by examiner

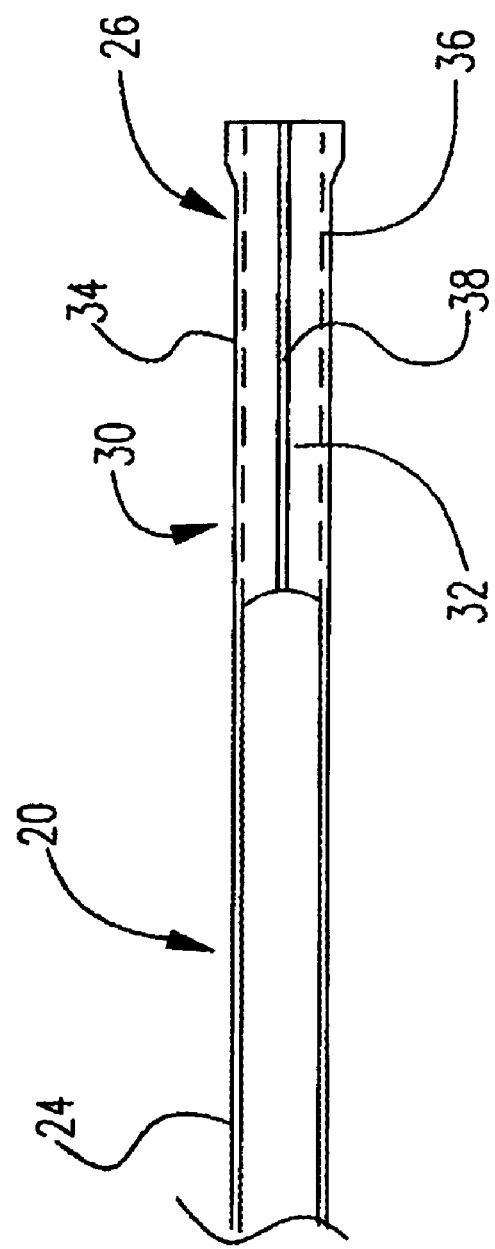

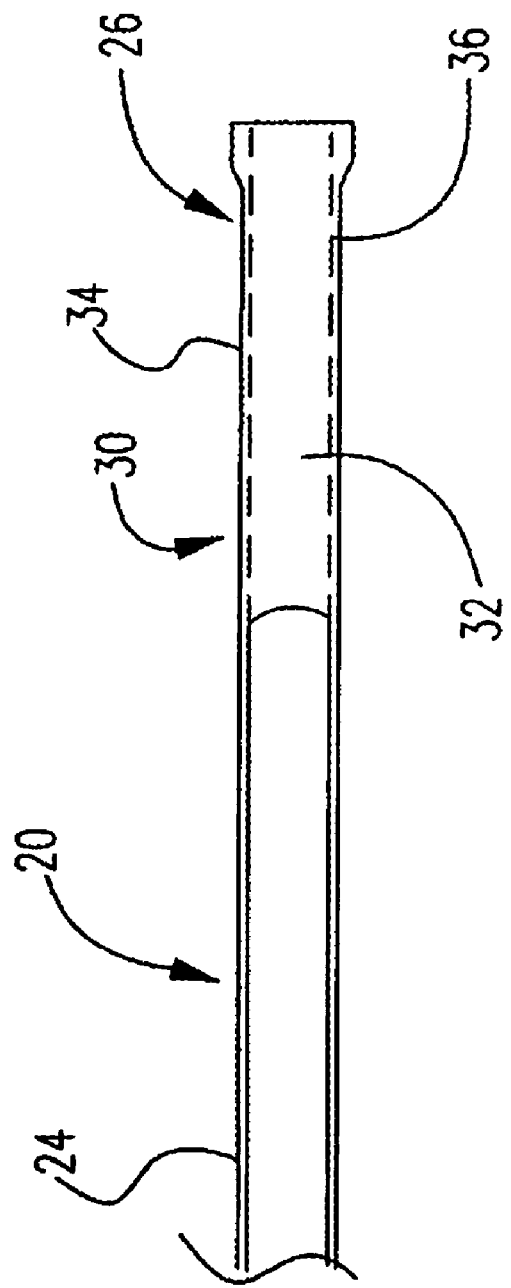

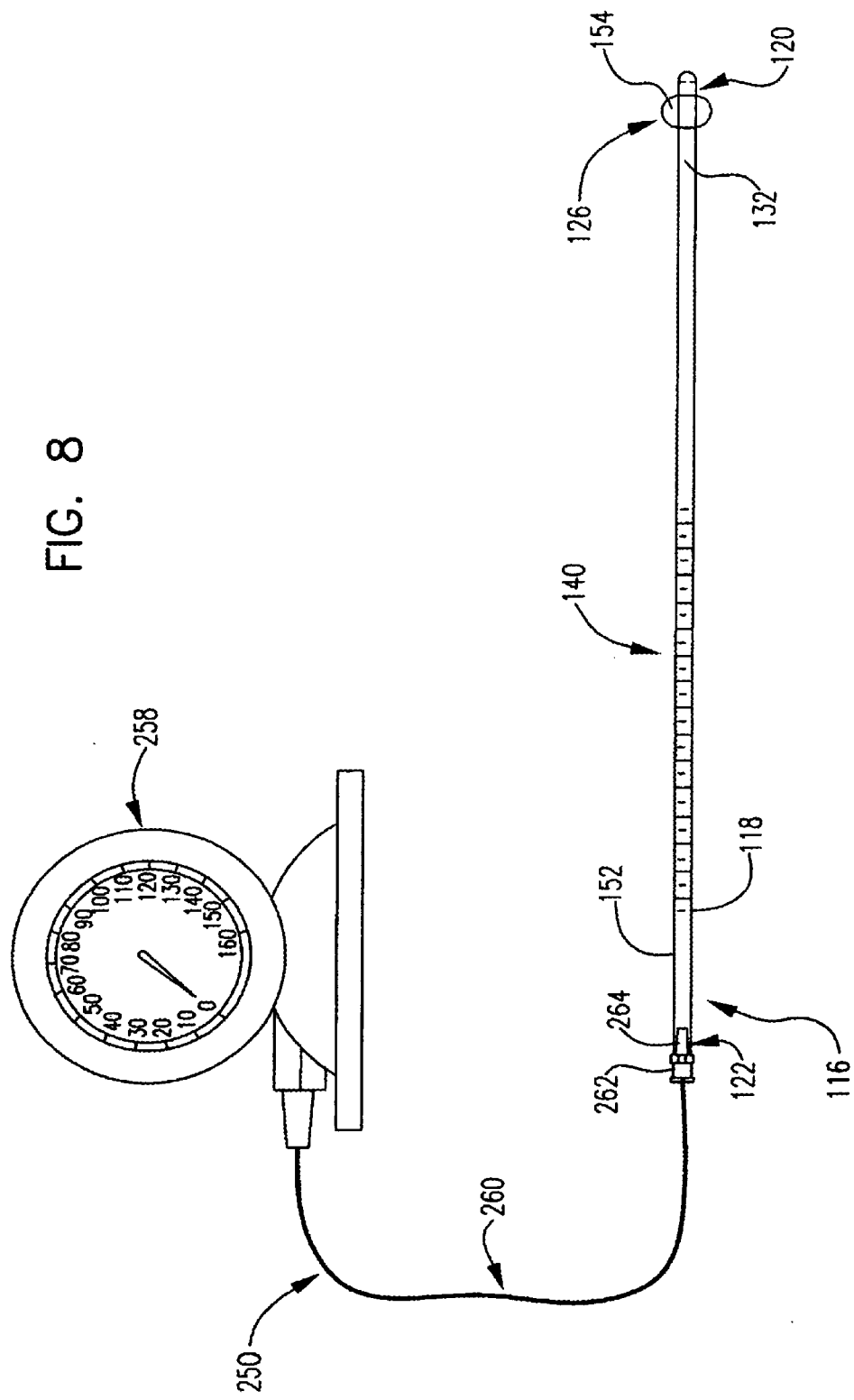

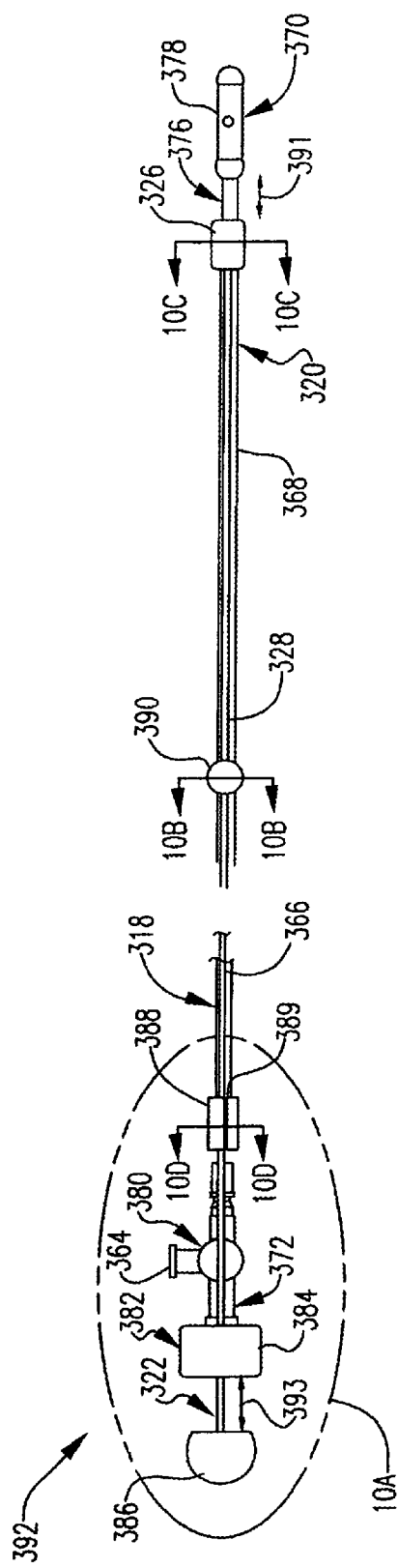

URETHRAL PROFILING DEVICE AND METHODOLOGY

This is a regular application filed under 35 U.S.C. §111(a) claiming priority under 35 U.S.C. §119(e) (1), of provisional application Serial No. 60/299,973, having a filing date of Jun. 22, 2001, and provisional application Serial No. 60/324,366, having a filing date of Sep. 24, 2001, both of which were filed pursuant to 35 U.S.C. §111(b).

TECHNICAL FIELD

The present invention relates to medical devices, more particularly, to devices, assemblies, and methodologies for profiling or measuring a body cavity, for instance a lower urinary tract and the architecture associated therewith in furtherance of assessing and selecting a remedial indwelling device.

BACKGROUND OF INVENTION

A diagram of the male urinary bladder and urinary passage (i.e., the lower urinary tract) is presented in FIG. 1. The bladder 400 temporarily stores urine 410 and periodically expels it when the bladder neck 420 opens, as the bladder 400 contracts. Urine 410 passes through the prostatic urethra 430, which is completely surrounded by the prostate 440. The distal portion or segment of prostate 440 is marked by a small projection called the verumontanum 450. This is a important landmark because distal thereto, is the external urethral sphincter 460, which relaxes prior to the urination process beginning. Beyond this is the bulbous portion 465 of urethra 470, affording a free passage of urine 410 external to the body, beyond the external urethral meatus 480.

Presently, millions of men in the United States alone exhibit some form of lower urinary tract symptoms (LUTS), with bladder outlet obstruction (BOO) being a major subgroup of LUTS. BOO is primarily caused by the enlargement of the prostate gland (e.g., benign prostate hyperplasia (BHP)) which results in radial compression of the urethra surrounded thereby (i.e., the prostatic urethra), thus obstructing (i.e., constricting) urine flow, resulting in incomplete emptying of the bladder (i.e., there being what is clinically referred to as a "post void residual" (PVR) of urine remaining in the bladder). Persons exhibiting an abnormal PVR will often need to urinate more frequently, and are likely to experience other physical discomfort, such as frequent urges to urinate, and physical exhaustion due to sleep deprivation, a condition clinically referred to as nocturia.

In addition to being symptomatic of BOO, the inability to pass urine (i.e., retention) may also occur due to loss of bladder function, or a depletion of normal bladder function which occurs in harmony with increased prostatic urethral resistance. Retention may also occur due to treatment of the prostatic urethra which often times causes a temporary swelling of the urethra until healing is complete. Such treatment includes the current standard of care for an enlarged prostate, referred to as trans-urethral resection procedure (TUR or TURP). Other treatments include minimally invasive debulking procedures such as trans-urethral microwave thermal therapy (TUMT), trans-urethra needle ablation (TUNA), prostatic alcohol injections, and cryogenic treatments. Patients are often times chronically in retention while awaiting any of these, or other clinical procedures. Some men will go into acute retention following unrelated surgeries such as hip surgery.

Another population of patients who frequently experience retention are those who have undergone minimally invasive or invasive cancer treatments for the prostate. When cancer is treated in the prostate two common options are radical prostatectomy, and brachytherapy. While the former approach involves the complete excising of the prostate, the later involves the injection of seed material into the prostate which is radioactive or excited by radiation, and thusly intended to selectively kill the cancer cells.

Patients suffering from reduced urine flow, incomplete emptying of the bladder, small volume urination, or combinations thereof, often require some interventional means to periodically drain or augment drainage of the bladder. Medical intervention of retention may include pharmaceuticals, minimally invasive procedures, prostatic support device insertions to support the prostatic region, or surgical interventions. Failure to take action can result in over distention of the bladder, leading to damage of the epithelium and detrusor muscles associated with the bladder, and an increased potential for urine reflux and bacterial invasion into the kidneys which is commonly thought to contribute to life-threatening renal failure.

Presently, the Foley catheter is the most common standard of care for obstruction treatment. A Foley catheter may be fairly characterized as being a tube having a pair of lumens extending therethrough, one of the lumens being used for inflation of a "balloon" supported adjacent a free end thereof, and of a relatively smaller diameter than the other. The free end of the Foley catheter is received within the external urethral meatus, and fed through the urethra until the balloon is positioned in the bladder. Thereafter the balloon is filled with sterile saline so as to expand (i.e., increase volume). Having been filled with anywhere from about 4 to 10 cc volume, the Foley catheter is then retracted until the balloon comes into contact with the bladder outlet. The nurse or physician then knows that the device is properly placed by tactilely sensing the abutting engagement of the balloon with the bladder neck.

Although catheterization is widely used to drain the bladder, it is sometimes clinically more desirable to place an indwelling device to support the prostatic urethra to relieve retention, or an excessively severe obstruction. This too has its shortcomings.

It is generally believed that the current options for sizing prostatic support devices are more complex, costly, and invasive than is required for proper device selection. One sought after sizing measurement is readily ascertained by tactilely detecting the location of the bulbous urethra relative to the bladder outlet. As previously noted, the bladder outlet is tactilely located whenever a Foley catheter is properly deployed. For proper placement of an intraurethral support device so as to assure that the external sphincter is not held open, the distance from the bladder outlet to the external sphincter must be determined. This may be acquired easily due to the fact that there is a second convenient anatomical feature which may be detected during measurement. The external sphincter is located at the bladder side of the bulbous urethra. The bulbous urethra is a very pronounced anatomical feature in that there is considerable widening of the urethra in this region. If a sound (i.e., Bougie) or a catheter is introduced into the urethra and advanced, contact with the external sphincter is easily detected therewith (i.e., tactilely with the hand).

Beyond notions of intervention, in roads are presently being made in the area of office and office/home based monitoring of patients for purpose of diagnosing the contribution of the prostatic urethra to the outflow urodynamics. Differential diagnosis is understood by accepting that there are three primary anatomical organs which interact to contribute to the function of urination: first the bladder, second the urethra, and third the sphincters. As previously noted, the prostatic gland surrounds the urethra in the very short segment between the bladder, at its outlet, and the external sphincter.

As bladder outlet obstruction patients are a subgroup of patients with LUTS, proper treatment of the specific problem requires a knowledge of complete urodynamic status of the patient in order determine the cause of the symptoms. Causes may include bladder deficiencies such as bladder decompensation or hypertrophy, sphincter dysnergia, prostatic obstruction, urethral lesions and others.

There exist diagnostic procedures available to clinical urologists, the purpose of which is to assess the physiologic properties of the lower urinary tract and symptoms related thereto. Such tests, which address the filling/emptying conditions (i.e., dynamics) of the bladder, include, but are not limited to, the use of video fluoroscopy simultaneously with the holding and release of urine, cystometry, urethral pressure profiling, ultrasonic volume assessments, and uroflowmetry. In addition to the aforementioned utility of sizing prostatic support devices and the like, the subject invention provides additional heretofore unknown diagnostic options which allow for relatively simple and increased understanding of the urinary tract by assessing the elements (i.e., structures or architecture) thereof, more particularly the prostatic urethra and their influence on urine flows.

SUMMARY OF THE INVENTION

A urethral profile apparatus, assembly and appurtenant methodology is provided. The apparatus includes an elongate member having proximal and distal ends, the proximal end including a probe. The probe is selectively positionable within a urethral passageway by axial translation of the elongate member via the distal end, with the probe dimensioned so as to indicate constrictures of the urethral passageway.

The endourethral assembly preferably includes a urethral profile apparatus adapted so as to be supported by a catheter. The urethral profile apparatus in turn includes a probe dimensioned so as to tactilely indicate constrictures of a urethral passageway, the probe being carried by a portion of the catheter for axial translation with respect thereto.

Finally, in a method of urethral profiling, a probe is introduced into a portion of the lower urinary tract, the probe being configured so as to indicate constrictures of the lower urinary tract. Thereafter, tactile sensing of the engagement of the probe with the constrictures of the lower urinary tract are completed, with indication made to a discrete point on a distal segment of the probe for comparison with a benchmark upon tactile sensing of engagement of the probe with the constrictures of the lower urinary tract so as to ascertain the distance between the external sphincter and the bladder neck. More specific features and advantages will become apparent with reference to the DETAILED DESCRIPTION OF THE INVENTION, appended claims, and the accompanying drawing figures.

BRIEF DESCRIPTION OF THE DRAWINGS

FIGS. 5A–5C illustrate alternate proximal segments for the apparatus of FIG. 2;

FIGS. 6A–6C illustrate details of the marker of FIG. 3;

FIG. 8 depicts the apparatus of FIG. 7 wherein the monitoring element is a pressure indicating assembly;

FIG. 10 illustrates a further embodiment of the urethral profile apparatus of the subject invention in combination with a guiding catheter;

FIG. 12E' depicts the profiling step of FIG. 12E utilizing a urethral profiling apparatus having a dilatable probe.

DETAILED DESCRIPTION OF THE INVENTION

The urethral profile apparatus of the subject invention generally includes an elongate member having proximal and distal ends, the proximal end including a probe. The probe is selectively positionable within a urethral passageway by axial translation of the elongate member via the distal end, the probe being dimensioned so as to indicate constrictures of the urethral passageway. The several embodiments of the subject invention, namely those of FIGS. 2, 4, 7, 8, 10 & 11, will be separately described hereinbelow.

Figure 1:
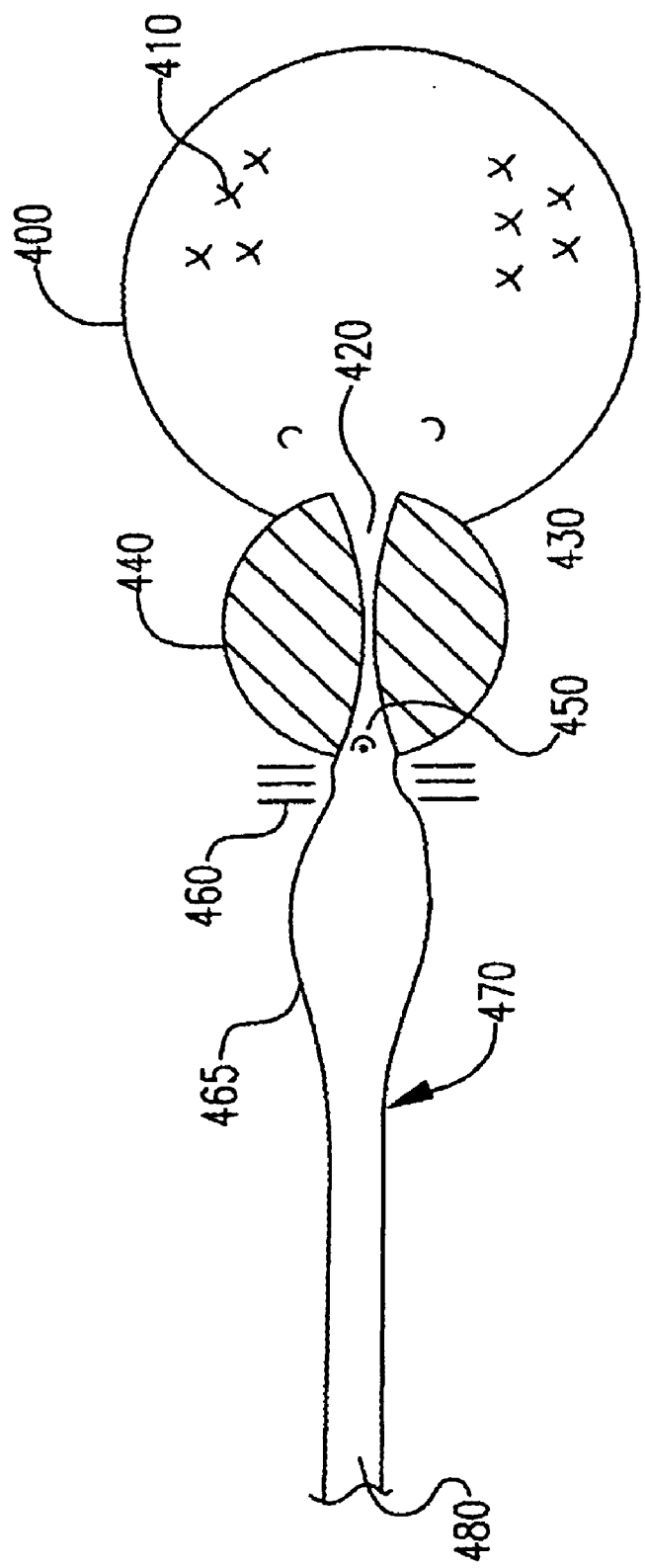
FIG. 1 depicts the human male urinary bladder and urinary passage.
Figure 2:
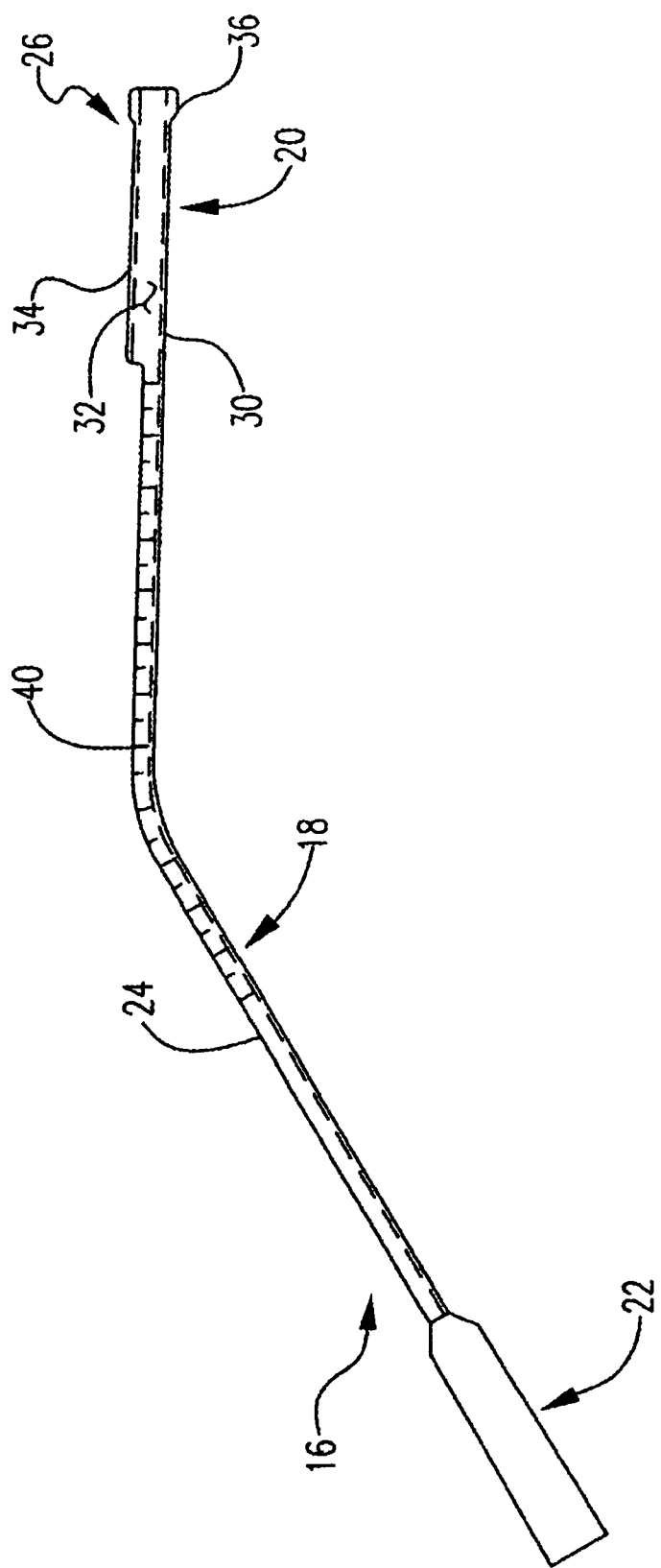
FIG. 2 illustrates a urethral profile apparatus of the subject invention.
Figure 3:
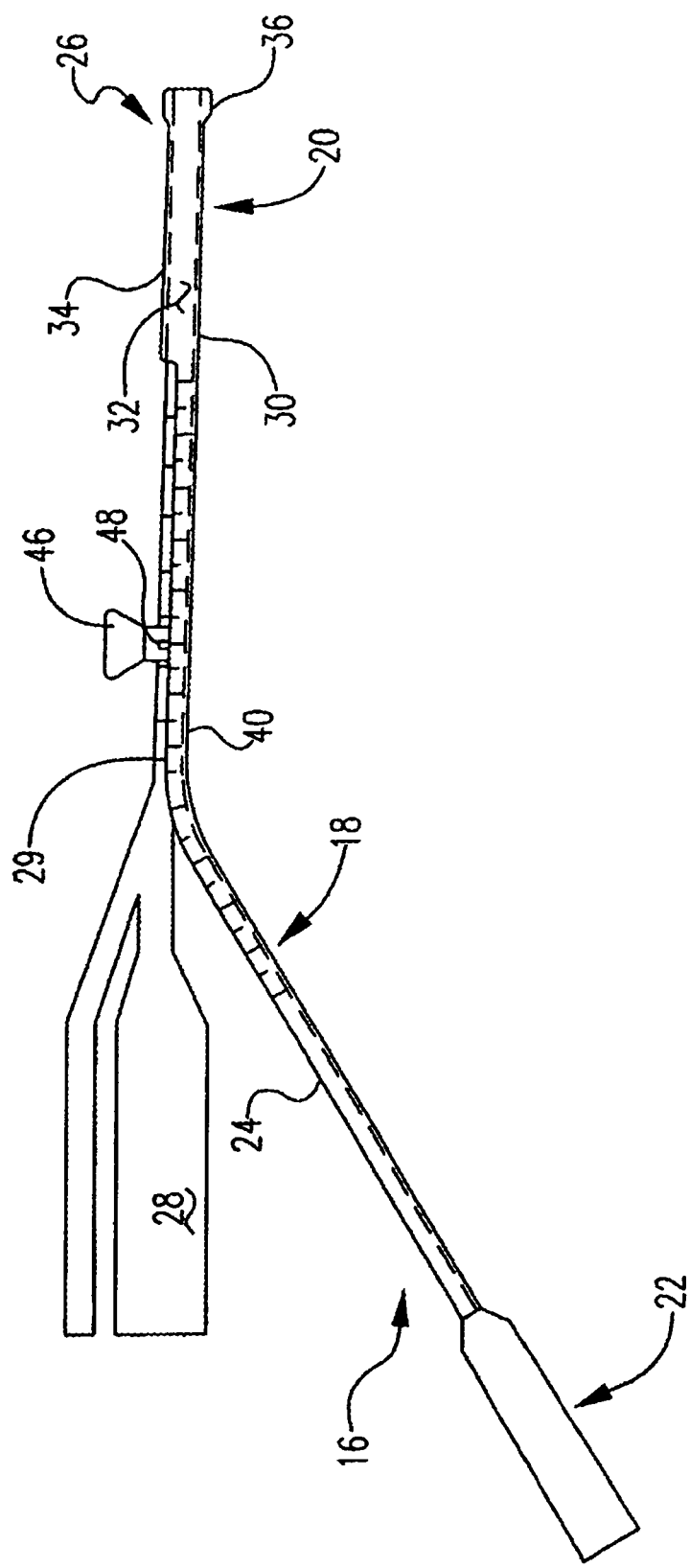
FIG. 3 illustrates the urethral profile apparatus of FIG. 2 in combination with a catheter.
Figure 4:
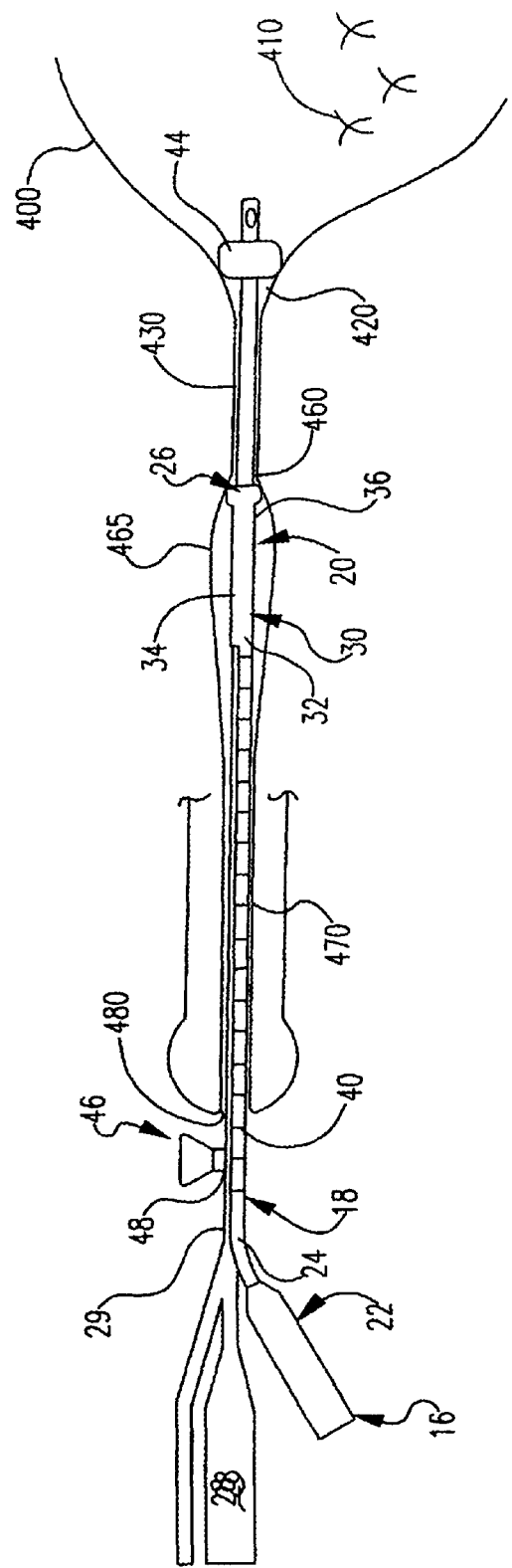
FIG. 4 illustrates the assembly of FIG. 3 indwelling within the urethral passageway of FIG. 1.

Referring generally to FIGS. 2–4, the urethral profiling apparatus 16 includes an elongate member or body 18 having a proximal end or extremity 20 and a distal end or extremity 22. As shown in the figures, a portion 24 of body segment 18 linking the proximal and distal portions is preferably, but not necessarily, configured as an open channel for reasons that will become apparent as this discussion proceeds.

The proximal extremity 20 of the elongate member 18 includes a probe 26 which is selectively positionable within the urethral passageway by axial or longitudinal translation of the elongate member 18. More particularly, the probe 26 is adapted to be received upon a catheter 28, the probe 26 thereby being translatable along at least a segment thereof, as by reciprocation of the distal portion 22 of the body 18. The catheter 28 performs a support and guide function for the urethral profile apparatus 16, more particularly the probe 26 which is sized and configured so as to indicate constrictures of the urethral passageway, as for instance by being rigidly dimensioned so as to enhance the tactile experience of the urethral profiling. A resiliently responsive probe, or probe that is reversibly expansive also has utility, and is contemplated for the subject invention.

The proximal portion 20 of the body 18 preferably comprises a tubular member 30 which is receivable on the catheter 28 (FIGS. 3 & 4) such that the urethral profile apparatus 16 is capable of pre-loading (FIG. 3) there upon for subsequent urethral insertion and exploration (FIG. 4). More particularly, the proximal portion 20 includes an exterior wall or wall portion 32 which defines a passageway 34. Passageway 34 is configured and dimensioned so as to allow for an end of a standard Foley catheter to be received therein.

Foley catheters are normally available in 2 French size intervals from as small as 8 French, to as large as 26 French. The urethral profile or measurement apparatus may be provided in a variety of sizes to interact with any of these sizes, with the preferred Foley catheter size range being 16 to 18 French. The necessary clearance between the proximal extremity passageway 34 and the Foley is a minimal of 0.004", and preferably at least 0.015". The diameter requirement of the probe 26 of the proximal extremity 20 of the measurement device is a minimum of 2 French greater than the Foley diameter, and more preferably 4 French (i.e., approximately 0.052"). It is common to introduce within a male urethra cystoscopes with outer diameters as great as 38 French. Outer profiles of the proximal extremity 20 will be 38 French and smaller. It should be noted that the use of larger devices within the urethra are more traumatic than smaller ones, and cause more bleeding. Although the male urethra bleeds easily, it quickly stops, however, less trauma and bleeding is always preferable.

Figure 5A:
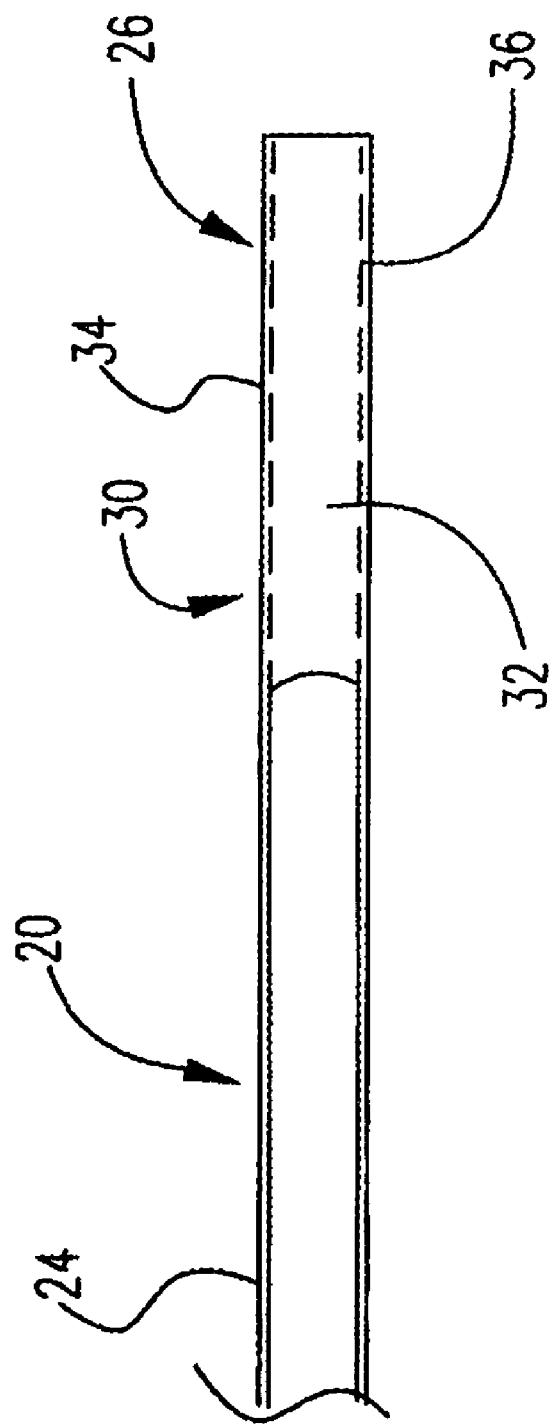

Referring now also to FIGS. 5A–5C, the probe 26 is preferably integral to the tubular element 30, the probe 26 comprising a portion or segment 36 of a free end of the tubular element 30. For instance, the probe 26 may include an enlarged end portion of the tubular element (i.e., a portion of increased cross-section, e.g., a belled end), such configuration being beneficial as an aid to tactilely sensing architectural changes within the urethral passage and permitting same in a least traumatic manner (compare FIG. 5A with FIGS. 5B & 5C). The important characteristic is that the probe 26 be dimensioned and/or of a material that is responsive to constrictures of the urethral passageway, and that the probe 26, or a leading edge thereof, be "tissue friendly" (i.e., configured so as to minimize tissue trauma).

A further advantageous or desirable feature of the urethral profiling element is that of easy disengagement thereof from the catheter, especially in applications wherein the catheter is to remain indwelling. Generally, the tubular element 30, more particularly the wall 32 thereof, is adapted to be easily received and removed from the catheter.

In addition to having tubular elements with a continuous circumferential wall, FIGS. 5A & 5C, the tubular element 30 of the proximal end 20 of the apparatus 16 may include a longitudinal slot or slit 38 in the wall thereof, FIG. 5B, which permits receipt of the urethral profiling apparatus 16 on an indwelling catheter (i.e., as opposed to pre-loading a catheter with a device having a tubular element as FIG. 5A or 5C). Furthermore, the tubular element styles of FIGS. 5A & 5C may also include a line of weakness (e.g., score line, perforation, etc.) extending through at least a portion of the element's length in furtherance of device removal from the catheter, alternately, the tube/apparatus may be simply cut off of the catheter. Such tear away configuration, fold away configuration, or solid tube configuration may be incorporated with either a straight tube or enlarged bulb architecture at the proximal extremity 20. The slit, or tear-away may be either straight along the longitudinal axis as previously noted, or alternatively may be provided in a helical, semi-helical, serpentine, or other configuration which enhances the durability of the slit in sliding along the axis of the Foley catheter without premature release during use.

With reference especially to FIGS. 3 & 4, the urethral profiling apparatus 16 is shown in a supported condition, received upon a Foley catheter 28, thereby defining an endourethral assembly. At least a portion of the body 24 of the urethral profiling apparatus preferably includes graduations or markings 40, more particularly the open channel segment of the body 24. These markings, in combination with at least a single mark or set of spaced apart marks 29 on the catheter 28 (i.e., the benchmarks), permit measurement of the features of the lower urinary tract (i.e., ascertainment of the distance between the bladder neck 420 and the external sphincter 460) as will be subsequently detailed.

The Foley catheter 28 is illustrated with "balloon" 44 inflated at the bladder outlet 420 (FIG. 4). The urethral profiling apparatus 16 is in a position such that the proximal extremity 20 is touching the urethra in the region of the external sphincter 460. There is a natural widening of the urethra at a location just distal of the external sphincter urethral region. This widening delimits the bulbous urethra 465.

Figure 6A:
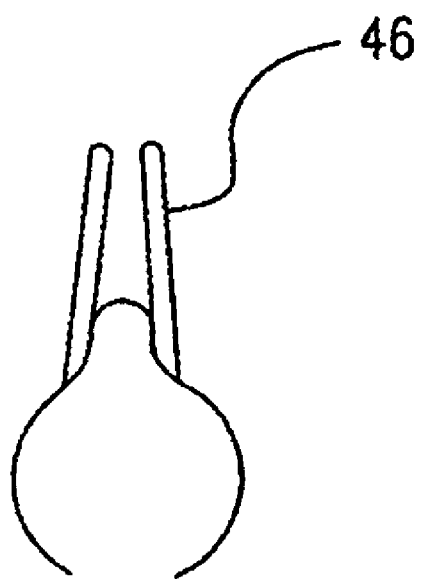
Figure 6B:
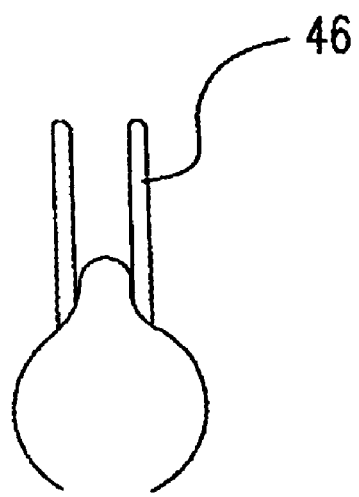

As the apparatus 16 is advanced over the Foley catheter 28, it may be appreciated from the illustration that any narrowing of the urethral passageway (e.g., that associated with the transition from the bulbous urethral 465 to the external sphincter 460) may be tactilely identified by the advancing probe 26. A marker 46 (e.g., a spring clip bearing a notch or other discernable reference mark 48, as illustrated in FIGS. 3 & 4, and detailed in FIGS. 6A–6C) may then be positioned in gripping engagement upon on the Foley catheter 28, in the vicinity of the meatus 480, to memorialize the detection of any narrowing of the urethral passageway. By comparing the location of marker 46 (i.e., the reference mark 48 thereof) with indexed body markings 40 of the apparatus, and/or with those of the benchmark (i.e., the mark or markings 29 of the catheter), the distance from the bladder outlet to the most distal location of the external sphincter may be determined. The Foley catheter may be left in place or removed, dependent upon the needs of the patient. If the catheter is to be removed, the measurement apparatus may be removed with the Foley. Measurement may be achieved directly in this instance even without the use of marker 46 as the relative position between the markings of the apparatus and those of the catheter need only be noted, the distance between the anchoring balloon 44 and the catheter markings 29 being known and fixed, and thereby defining a benchmark against which or from which the lower urinary tract structural relationships may be determined.

Figure 7:
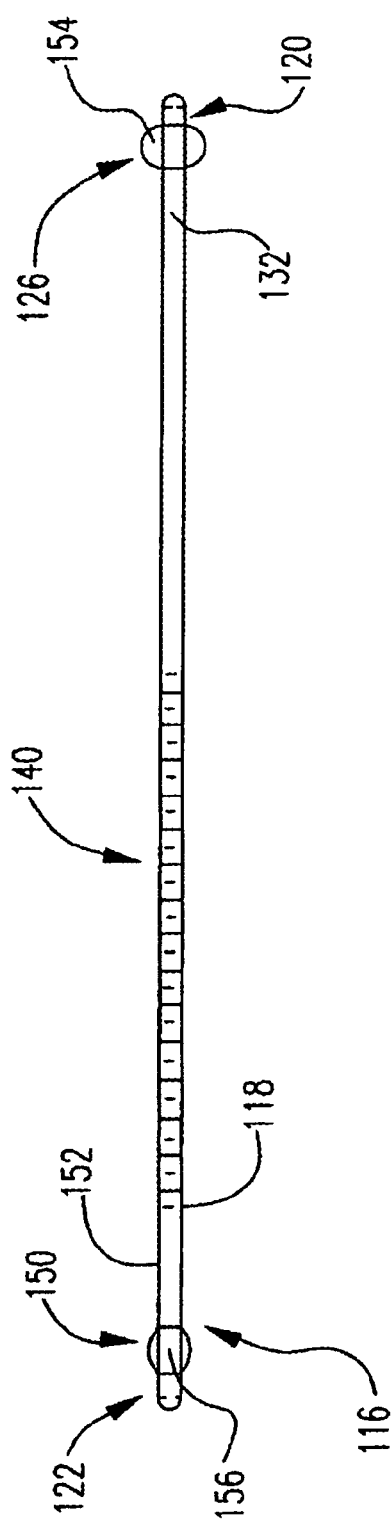
FIG. 7 illustrates a further embodiment of the urethral profile apparatus of the subject invention, more particularly a self-guiding apparatus.

Referring now to FIGS. 7 & 8, alternate self-guiding embodiments of the subject invention are illustrated, concurrent use of a catheter not being required. The urethral profile apparatus 116 of this embodiment generally includes an elongate member or body 118 having a proximal end or extremity 120 and a distal end or extremity 122. The proximal extremity 120 of the elongate member 118 generally includes a probe 126 which is resiliently responsive to constrictures of the urethral passageway, preferably comprising a reversibly expandable element (e.g., a balloon or the like) circumferentially disposed about a segment of the proximal end of the elongate member. The distal extremity or end 122 of the elongate member 118 includes a monitoring element 150, the monitoring element being in fluid communication with the probe 126 such that the monitoring element 150 is responsive to forces bearing upon the probe 126 as will later be explained.

The body 118 of the urethral profile apparatus 116 is preferably tubular in configuration, having at least a single lumen 152 therethrough, and extending between the proximal 120 and distal 122 ends thereof. Both the probe 126 and the monitoring element 150 are in fluid communication with the lumen 152 (i.e., a lumen at least indirectly joins or connects the probe 126 to the monitoring element 150), a closed fluid system being thereby defined. The proximal end 120 of the body 118 includes at least a single proximal body aperture 154 for the ingress/egress of fluid between the lumen 152, at the proximal end 120, and the probe 126 overlaying the proximal body aperture or apertures 154. At least a portion of the tubular body 118 includes spaced apart measuring indicia 140 (e.g., linear graduations), with such measuring indicia being applied or generally carried upon a surface, or otherwise integral to, part of a wall 132 of the body 118.

Referring now specifically to FIG. 7, this apparatus embodiment is show in a static, "out of the box" condition. Each of the terminal ends of the body 118 of the urethral profiling apparatus 116 are preferably closed, and characteristically rounded. The monitoring element 150 preferably comprises a reversibly expandable element, structurally comparable to that comprising the probe 126, overlaying at least a single distal body aperture 156 for the ingress/egress of fluid into/from the lumen 152.

The reversible expansive elements (e.g., balloons) of the proximal 120 and distal 122 ends may be filled by simply introducing fluid into the body lumen 152, for instance through the proximal or distal extremities of the device which may be adapted or otherwise constructed for such purposes. The extremities of the apparatus are preferably, but not necessarily, formed from medical grade silicone, this material being self sealing after fluid injection, as by hypodermic needle. When a total system volume of from about 3 to 10 cc, and preferably 5 cc, is introduced into the generally closed system, both balloons will be partially inflated. The balloons are selected to be at a low interior pressure during "full" volume so that the fluid may easily be shuttled between the two balloons. Although the subject apparatus is preferably pre-filled and pre-sterilized, pressurization and sterilization prior to use at the clinic etc. is equally plausible.

Characteristic of the static condition for the apparatus 116 is the probe 126 being at a relative volume maximum and the monitoring element 150 being at a relative volume minimum. Such relative minimum/maximum volume characteristics for the balloons of the monitoring element 150 and probe 126 may be obtained by having balloon materials of different durometer, identical balloon materials of different wall thickness, or non-congruous balloon dimensions, such static condition for the apparatus being considered within the providence of a person of ordinary skill in such science.

Referring now specifically to FIG. 8, this apparatus embodiment includes a monitoring element 250 comprising a pressure indicating assembly. Equally advantageous in lieu of the pressure indicator shown is a pressure/volume sensor in combination with a recording device, whether it be analog or digital. A healthy male urethra will dilate at less than about 50 centimeters of water pressure.

As illustrated in FIG. 8, the pressure indicating assembly 250 includes a pressure gauge 258 which is connected to the urethral profile apparatus 116 via a pressure line or tube 260. The pressure line 260 is provided with a male luer fitting 262 which connects to a barbed female luer fitting 264 which is mounted (i.e., received) in the lumen 152 at the distal extremity 122 of the elongate member 118.

As with the embodiment of FIG. 7, it is important that the apparatus define a closed system (i.e., be non-atmospheric) and include a monitoring element 250 that is responsive to force bearing upon the probe 126. Charging (i.e., pressurization) of the probe 126 prior to deployment is readily accomplished via a one way fluid filling port integral to the apparatus, for instance built into the distal end 122 of the apparatus body 118.

Figure 9A:
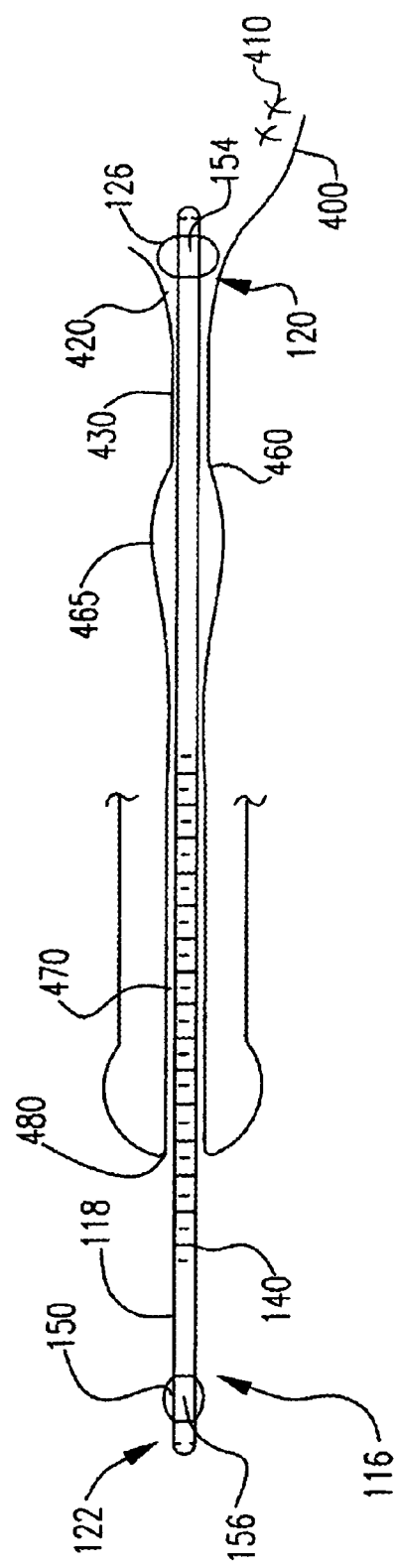
FIGS. 9A–9C illustrate a profiling methodology utilizing the apparatus of FIG. 7.
Figure 9B:
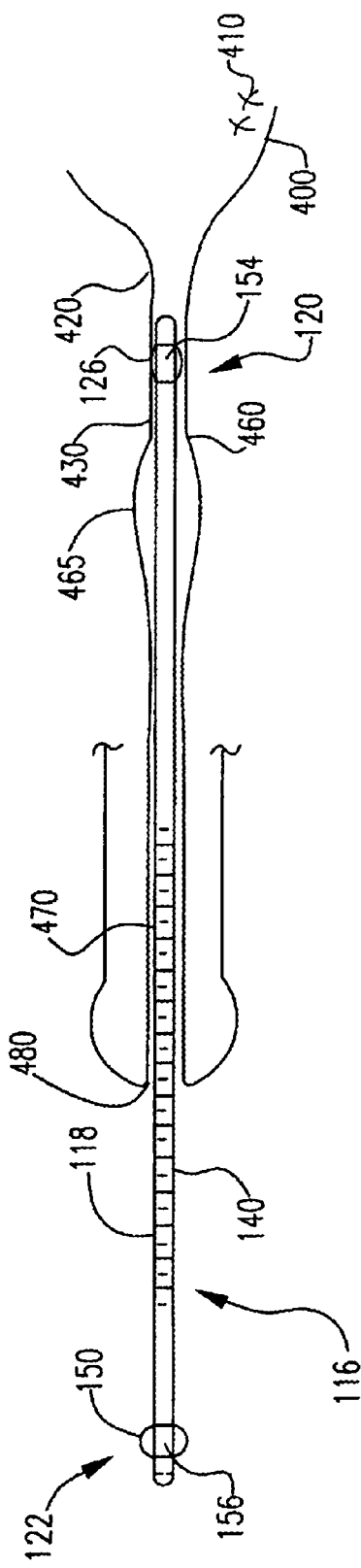
Figure 9C:
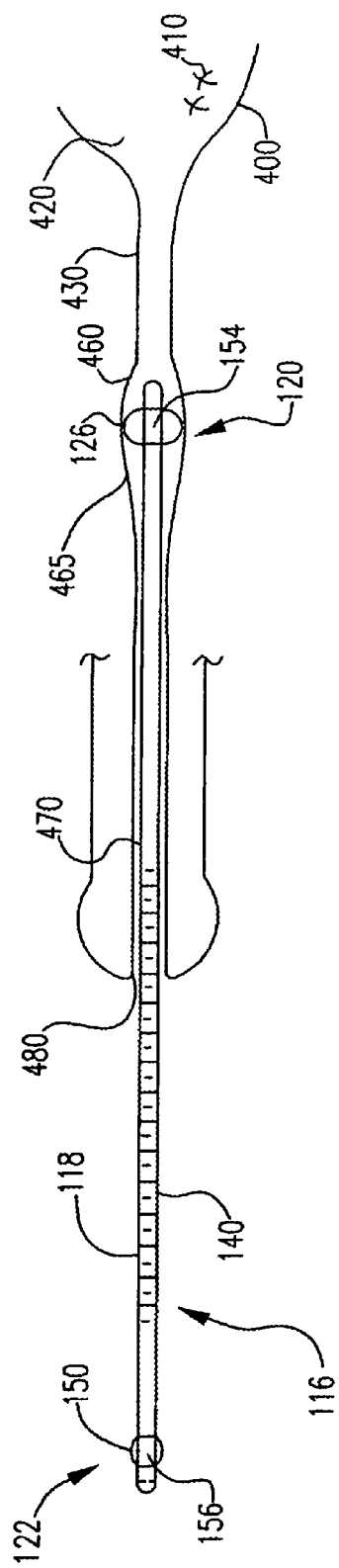

Referring now to FIGS. 9A–9C, the apparatus of FIG. 7 is illustrated in various states or conditions of urethral deployment in furtherance of profiling. Initial urethral positioning of the apparatus, with the probe 126 adjacent the bladder outlet as FIG. 9A, mimics the static condition for the apparatus (FIG. 7), namely the probe balloon 126 being at a relative volume maximum, the monitoring balloon 150 being at a relative volume minimum. The point of measurement which allows monitoring of the travel from the bladder outlet to the bulbous urethra may be the tip of the of the extended penis.

As the apparatus 116 is withdrawn from the penis, FIG. 9B, the fluid within the apparatus will begin to shuttle from the probe balloon 126 to the monitoring balloon 150. As the probe 126 passes into the prostatic urethra, the fluid therein will be mostly if not completely displaced and received in and by the monitoring balloon 150. As the probe 126 is further retracted, FIG. 9C, the fluid will again begin to shuttle from the monitoring balloon 150 to the probe balloon 126. By observing and recording the measurements as the fluid shuttles, the distance from the bladder outlet to the bulbous urethra may be determined. If the physician or urologists desires further tactile feedback, they may apply pressure to the monitoring balloon 150 at any point in the procedure to achieve a tactile understanding of the level of force (i.e., obstruction) that the probe balloon 126 is encountering. This may assist in more precisely identifying the architectural/anatomical transitions of the lower urinary tract. This is especially applicable at the bladder outlet as there exists less of an abrupt transition here than at the external sphincter.

The preferred material for the aforementioned embodiments of the subject invention is medical grade silicone or medical grade polyurethane. The reversibly expandable elements may be either of thin wall silicone, or alternatively, a thin walled, preformed, low compliance material such as polyurethane, thermoplastic elastomer (TPE), or polyethylene. As the subject invention is preferably for acute use, only short term exposure materials are necessary.

Figure 10A:
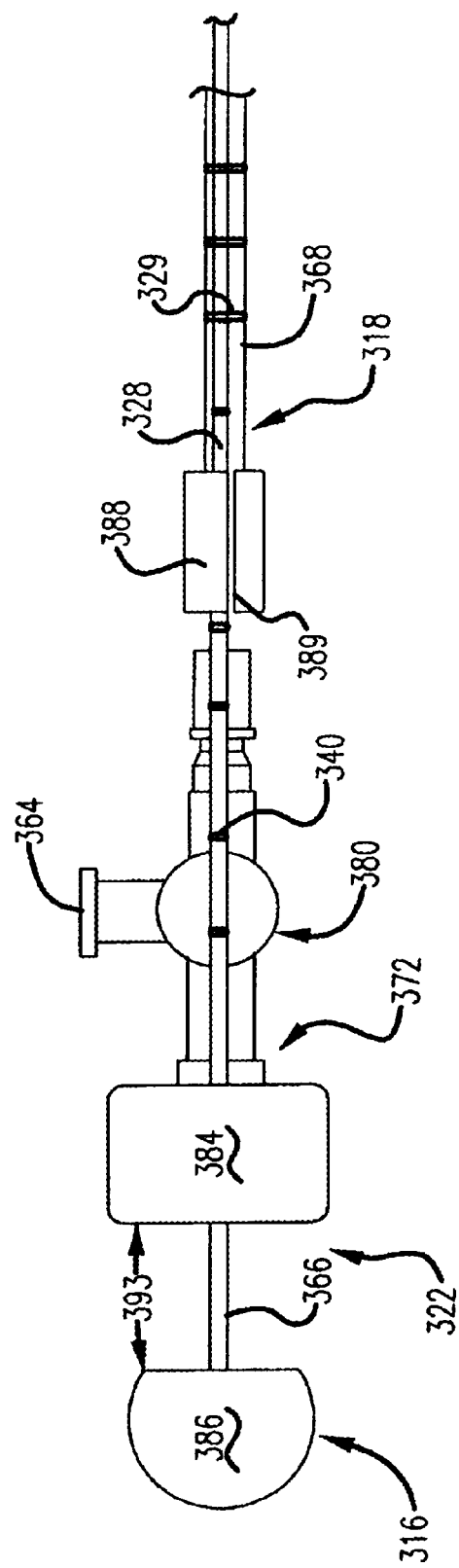
FIG. 10A is an enlargened view of the circled area of FIG. 10, more particularly the distal portion of the assembly of the subject invention.
Figure 10B:
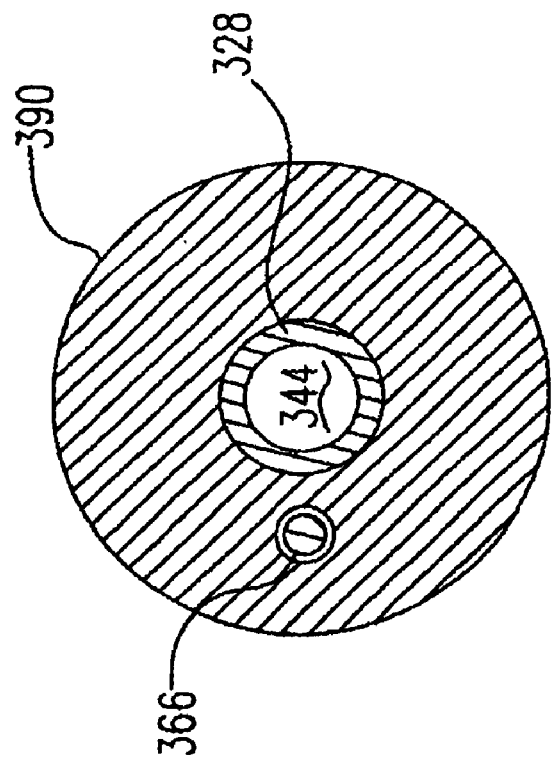
FIG. 10B is a sectional view about line 10B–10B of FIG. 10 showing a probe stop in section.
Figure 10C:
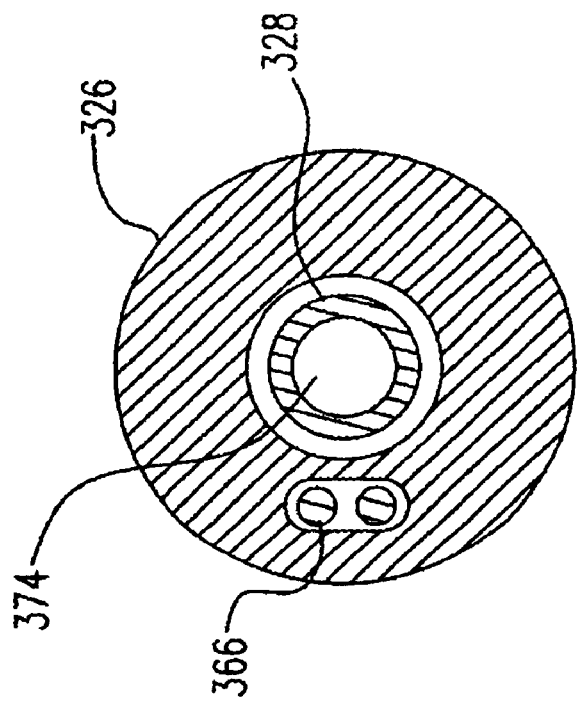
FIG. 10C is a sectional view about line 10C–10C of FIG. 10 showing a probe in section.
Figure 10D:
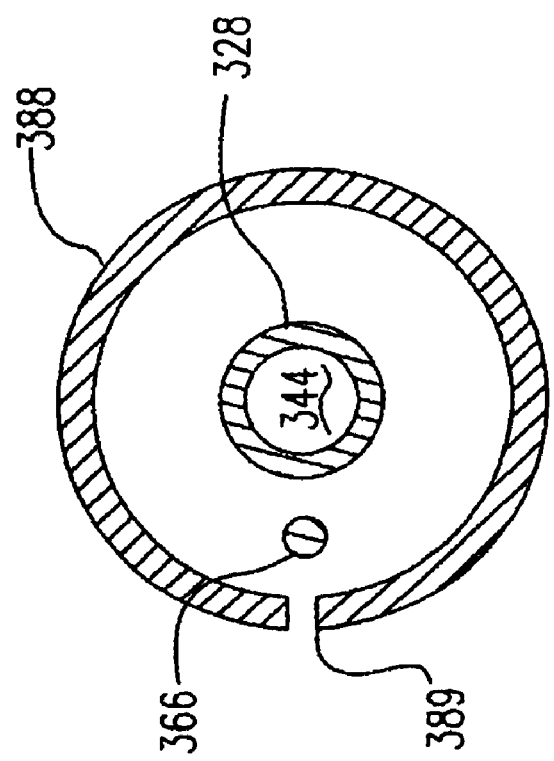
FIG. 10D is a sectional view about line 10D–10D of FIG. 10 showing the probe wire in section.
Figure 11:
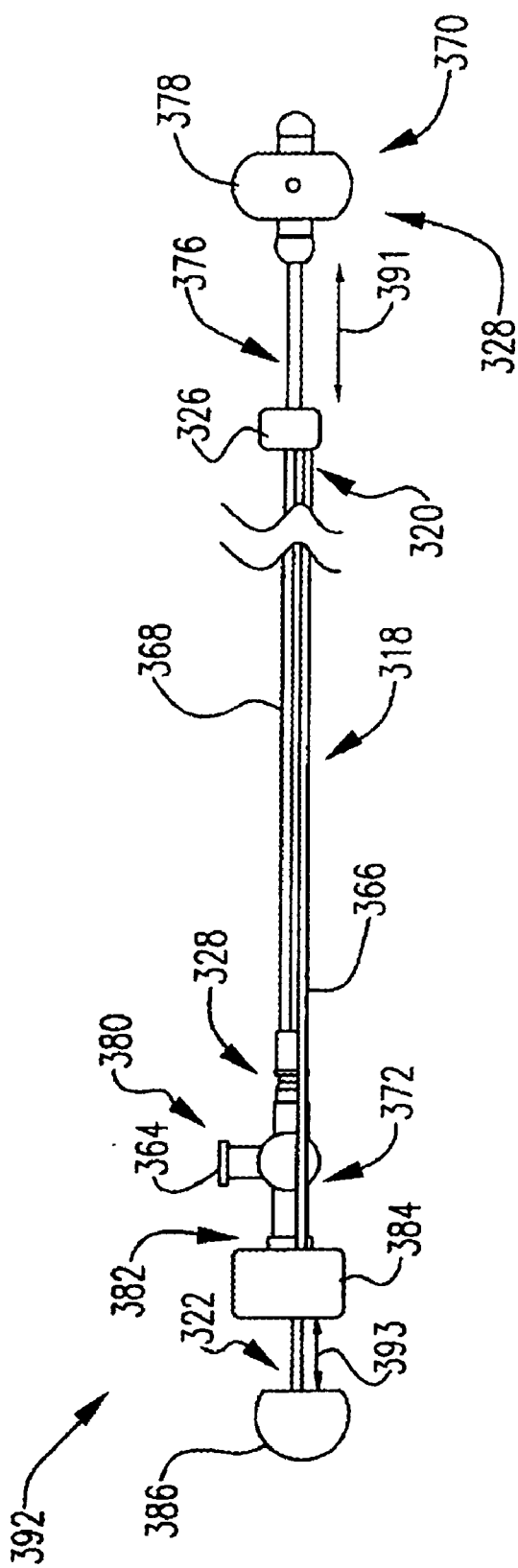
FIG. 11 depicts an alternate embodiment of the apparatus of FIG. 10.

Referring now to FIGS. 10 & 11, alternate catheter-guided embodiments of the subject invention (i.e., profiling assemblies) are illustrated. The urethral profile apparatus 316 of this style, shown guidingly supported by a catheter 328, generally includes an elongate member or body 318 having a proximal end or extremity 320 and a distal end or extremity 322. The proximal extremity 320 of the elongate member 318 generally includes a probe 326 which is selectively positionable within a urethral passageway by axial translation of the elongate member 318. More particularly, the probe 326 is adapted to be received upon the catheter 328, the probe 326 being axially translatable along a segment of the catheter 328 by a flexible probing wire 366 which includes spaced apart measuring indicia 340 (e.g., linear graduations). As prior embodiments, the probe 326 is configured and/or dimensioned so as to indicate constrictures of the urethral passageway.

Prior to further discussion of the subject embodiments, some discussion of the apparatus guide 328 (e.g., catheter)

is warranted. The catheter 328, as illustrated and well known in the art, generally includes an elongated body 368 having proximal 370 and distal 372 extremities, and a lumen 374 substantially traversing same. As in prior assembly embodiments, the catheter body 368 includes at least a single mark or set of spaced apart markings 329 (FIG. 10A) to serve a bench mark function as previously described with reference to FIGS. 3 & 4.

A proximal end segment 376 of the catheter 328 includes an anchor element 378, for instance a balloon circumferentially received or affixed to the a portion of the proximal end segment 376. The balloon may be inflated (FIG. 11)/deflated (FIG. 10) by ingress/egress of fluid therefrom. The balloon is in fluid communication with both the lumen 374 and a valve manifold 380 integral to a distal end segment 382 of the catheter body 368. The valve manifold 380 preferably includes a female luer port 364 and a hub 384. As will later be described, the anchor element 378 is received and positioned within the bladder such that the expanded anchor element abuttingly engages the a portion of the bladder.

A probe stop 390 (FIGS. 10 & 10B) is preferably part of the assembly 392, more particularly, the probe stop 390 is affixed to, integral with, or otherwise part of the catheter body 368 (FIG. 10C), e.g., as a radial projection from the surface thereof or as an encircling ridge or rim. The consideration here is that the probe stop limits the distal retraction (i.e., travel) of the probe 326 relative to the catheter 328. As shown, the probe stop 390 may further, but not necessarily, be adapted to slidingly receive the probe wire 366, thereby performing a secondary function as a probe wire support.

With continued reference primarily to FIGS. 10 & 10A, the urethral profile apparatus 316 includes the probe 326 (FIG. 10C) supported at a proximal end of the probe wire 366, and preferably, but not necessarily, includes a grip 386 supported at the distal end of the probe wire 366, an intermediate or supplemental probe wire support 388 (FIG. 10D), which removably encircles the probe wire 366 and the catheter body 368 (i.e., functions to maintain the spatial relationship between the probe wire 366 and the catheter body 368 in furtherance of longitudinal translation of the probe 326 relative to the catheter 328), and stop 390 (FIG. 10B) which as previously noted limits the retractability of the probe 326. The supplemental probe wire support 388 may be variably configured in known ways such that the probe wire 366 may freely pass therethrough, the support itself being preferably capable of select positioning or repositioning upon the catheter body 368. Positioning is facilitated by the inclusion of a slit or groove 389 which permits at least partial "opening" (i.e., spreading) of portions of the support 388 (i.e., the upper and lower left portions of FIG. 10D). A notch (not shown) for enhancing a hinge effect, and thereby support removal or relocation, may be included opposite the slit or groove 389.

As will become apparent with a discussion of FIGS. 12A–12E', when in combination with the catheter, (i.e., an assembly is formed) it is advantageously intended that the probe wire grip 386 of the assembly 392 be in abutting engagement with the hub 384 of the catheter 328 while the probe 326 abuttingly engages or is adjacent the proximal segment 376 of the catheter 328, that is to say, dimension 391 corresponds with (i.e., is substantially equivalent to) dimension 393. The axial travel of the probe 326, relative to the catheter 328, is proximally limited by a portion of a proximal end of the catheter, namely the anchor 378. Axial travel of the probe 326, relative to the catheter 328, is preferably distally limited by probe stop 390 (FIG. 10), or may be limited by a portion of the valve manifold 380 (FIG. 11) or other distal catheter structure.

The probe 326 (FIG. 10C) is preferably of rigid construction and is circumferentially or otherwise disposed about the catheter body 368 for sliding engagement with respect thereto (FIG. 10C). More particularly, and preferably, the probe 326 comprises a Teflon® ferrule into which an end of the probe wire 366 terminates.

The probe wire support 388 (FIG. 10D) generally receives therethrough both the catheter body 368 and the probe wire 366. Each element of the assembly 392, the catheter 328 and apparatus 316, is preferably free to travel with respect to the probe wire support 388 (i.e., is not encumbered thereby). Preferably the probe wire support 388 is adapted so as to be readily removed and reapplied from the assembly 392 as previously noted.

Probe stop 390 (FIG. 10B) is affixed to the catheter body 368 while being slidable along the probe wire 366. By this design, the stop 390 provides a limitation on probe retractability, as when the stop 390 abuts the distal extremity of the probe 326 (FIG. 10).

Figure 12A:
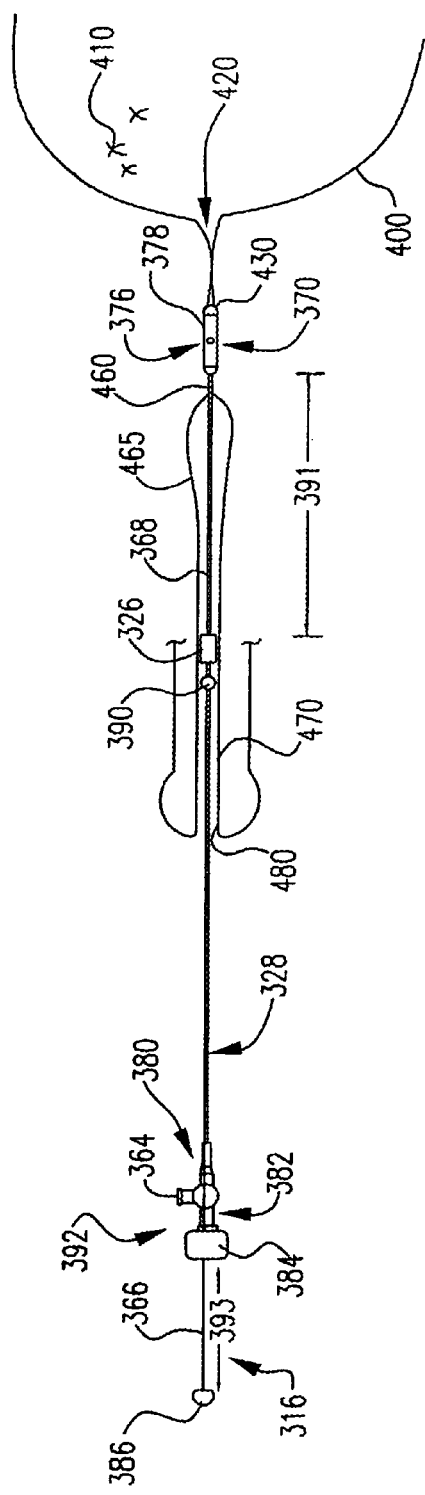
FIGS. 12A–12E depict urethral profiling utilizing the assembly of FIG. 10.

Referring now generally to FIGS. 12A–12E', the methodology appurtenant to the assembly 392 of FIG. 10 is generally illustrated. A proximal tip or end of the catheter 328 is introduced into the lower urethra through the interior of the penis. The proximal catheter tip is shown for the purpose of instruction on measurement in the multiple locations of FIGS. 12A–12E. The probe 326 is shown in FIG. 12A positioned within a portion of the urethra (i.e., the penile urethra), the anchor 378 of catheter 328 occupying the prostatic region 430 of the urethra, having passed through the external sphincter 460 which serves the physiological function of limiting urine flow from the bladder to the lower urethra, as by normally closing around and about the perimeter of the urethra until urination is desired.

The probe 326 is preferably, but not necessarily, fully retracted during assembly insertion. When the probe 326 is fully retracted, the resting position is against the stop 390. This is the preferred practice method in the clinical trials which have been currently performed. The urethral profiling apparatus 316 may alternatively be introduced with the probe 326 proximally translated (i.e., with the grip 386 of the probe wire 366 contacting the hub 384 of the catheter 328).

Figure 12B:
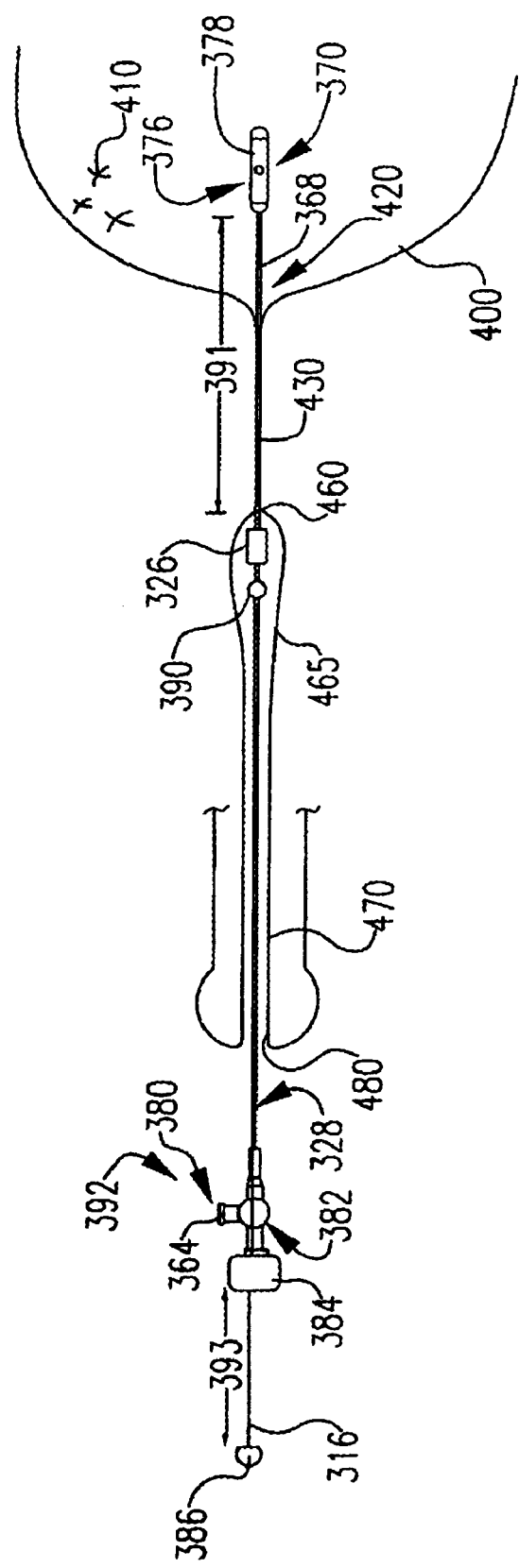

Referring now to FIG. 12B, the assembly 392 is illustrated in a condition of further advancement, such that the proximal catheter tip 370 is located or positioned in the bladder 400. It is noted that the prostatic urethra 430 makes contact against the catheter body 368. This contact may be "loose" if the patient's prostatic urethra is not compressive in nature from underlying hyperplasia (i.e., thickening), or other physiological condition.

Figure 12C:
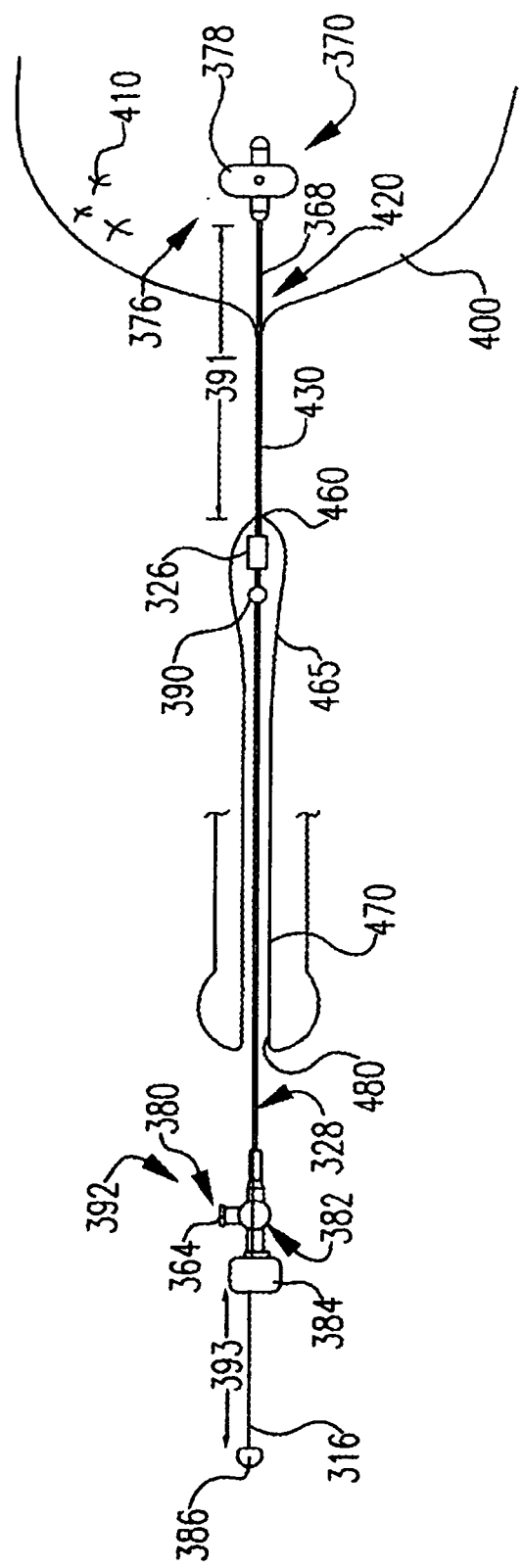

Referring now to FIG. 12C, the assembly 392 is shown as FIG. 12B, with the catheter anchor 378 in an expanded condition, in contemplation of assembly anchoring. This is accomplished by introduction of about 5 cc of sterile fluid into the female luer port 364 integral to valve manifold 380. The anchor 378 is oriented fully within the bladder at this time.

Figure 12D:
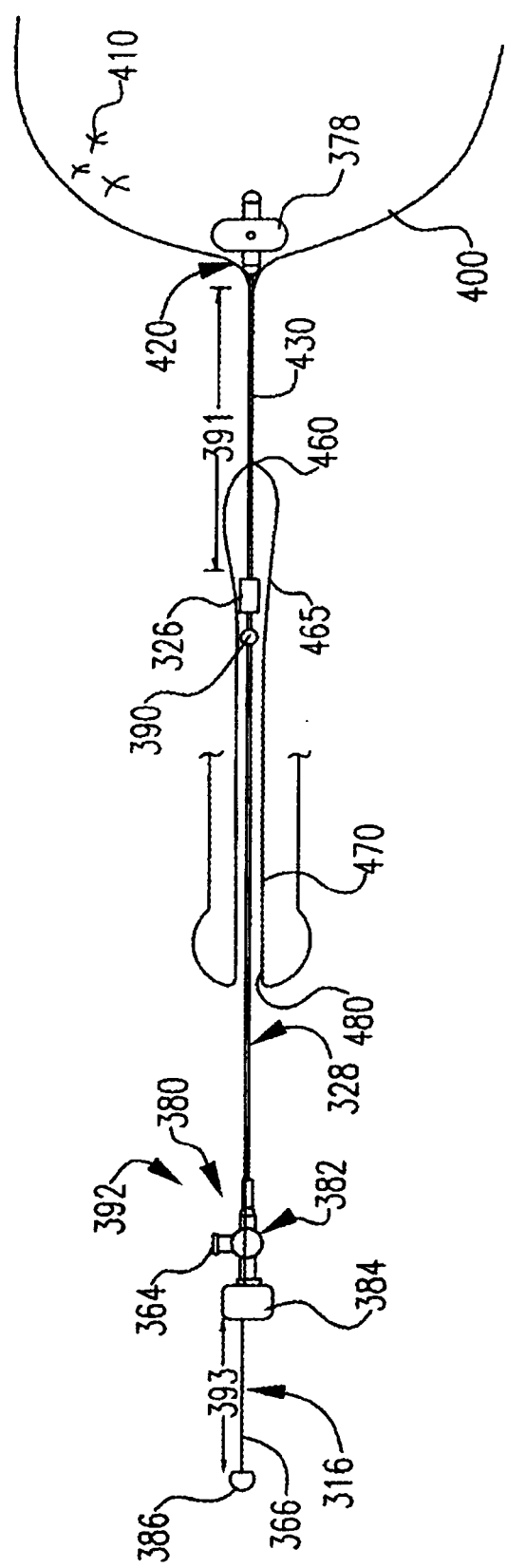

Referring now to FIG. 12D, the assembly 392 has been retracted from the FIG. 12C location. Retraction is accomplished using very low force, until the anchor 378 contacts and abuttingly engages the bladder outlet 420. When this occurs a strong tactile confirmation is easily detected by the practitioner conducting the procedure. As shown, the probe 326 remains within the urethra.

Figure 12E:
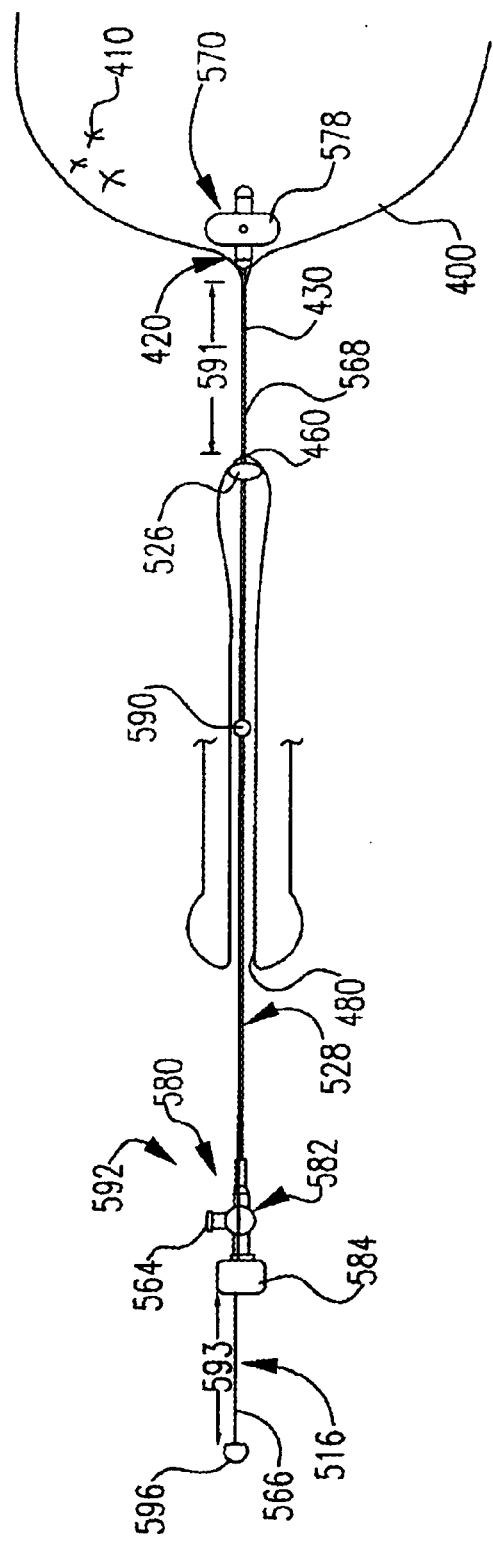
Figure 12E:
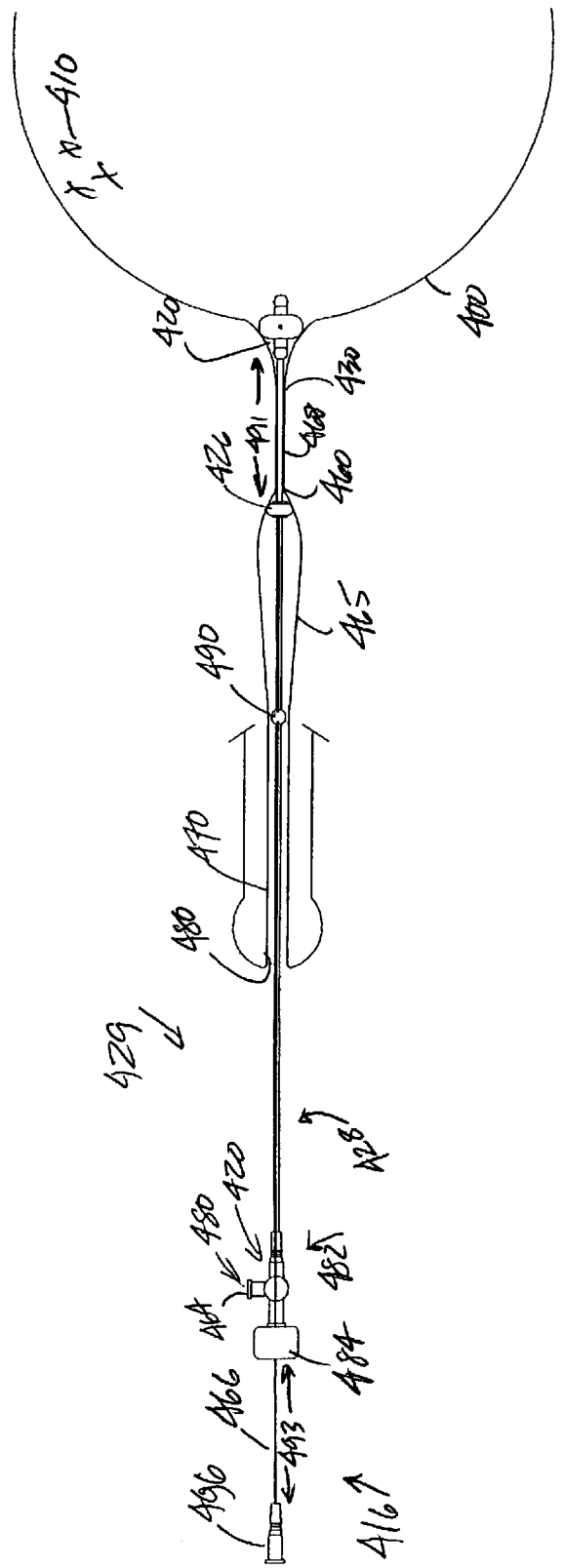

Referring now to FIG. 12E, the assembly 392 is illustrated with the probe 326 of the profiling apparatus 316 having been advanced proximally until it comes into contact with the external sphincter 460 of the urethra. As is shown, the urethra expands to a larger area just distal of the external sphincter, this region is commonly referred to as the bulbous urethra. When the probe 326 is advanced proximally, it passes from this large bulbous urethral region 465 to a tightly restrictive external sphincter region 460 of the urethra. The external sphincter 460 exerts sufficient pressure that when the probe 326 contacts the external sphincter 460, a further tactile feedback is felt by hand on the grip 386 of the apparatus 316. The probe wire 366 provides the longitudinal translation of force to the probe 326 which will flex when contact is made with the external sphincter 460.

The probe wire 366 is preferably comprised of 0.020" 304 stainless steel spring temper wire. The wire is sufficiently rigid to provide unencumbered advancement of the probe in the distal urethra when supported with the hand or wire support, and is sufficiently flexible to allow for flexure distal of the hub 384. This flexure allows ease of identification of the external sphincter because the bowing that occurs when contact is made with external sphincter makes identification of that contact simple. When the probe wire 366 is released, it will spring back to a straightened position.

As previously noted, the distance 393 between the probe grip 386 and the hub 384 corresponds exactly with the distance 391, the measured length from the bladder outlet 420 to distal of the external sphincter 460. By simply measuring this length, patient profiles may be easily attained. The measurement may include a manual measurement from a ruler, or caliper or apparatus with measurement utility, or alternatively, it may be easily appreciated that the measurement may be easily incorporated by applying gradients on the extremity of the probe wire 366 between the hub 384 and the probe grip 386. Gradients may be via spacing, color, or other useful differentiation which provides an indicator which is applicable to subsequent device or therapy selections. This measurement may then be applied to help assess the patient's needs.

Referring now to FIG. 12E', an alternate probe configuration is illustrated for the deployed assembly 392 of FIG. 12E. The probe 526 of assembly 592, as opposed to that of FIGS. 10 & 11, is reversibly expanded by the introduction of fluid into the proximal luer port 596 which is attached to a hollow probe support 566 (i.e., elongate element or member). This allows for introduction of the probe 526, which ranges in size according to the physicians selection from about 18 to 26 French, within the urethral passageway in a collapsed condition, with a diameter of as small as about 14 French, with subsequent expansion to a size as large as desired to assure there is tactile feel of the external sphincter. Practically, the male urethra has the greatest interior area near the bulbous urethra. This location rarely would be expanded without injury to greater than 44 French. Expansion of a dilatable probe beyond 30 French would rarely be practical or useful. Introduction of approximately 1 cc of incompressible fluid into the interior dilatable probe 526 provides this diameter and sufficient tactile feel of the external sphincter.

The prior steps of introduction of the embodiment of FIG. 12E' are identical to those of the prior embodiments (i.e., FIGS. 12A–12D). The reversibly expandable probe feature for the apparatus 516 provides particular utility for patients who have sensitivity in the urethra to the introduction of larger devices. Secondly, those patients with responsive external sphincters are more difficult to tacitly sense the external sphincter/bulbous urethra region, with the apparatus/assembly of FIG. 12E' providing greater comfort in the introduction and/or greater profile on the dilator. It may be further appreciated that the dilatable probe apparatus requires and provides for a mechanism to moving fluid to and from the probe 526. When pressure within the probe 526 is monitored (i.e., as the embodiment of FIG. 9), there is further non-tactile data available. When the expansible probe 526 is advanced into the external sphincter, a natural pressure rise occurs in the fluid system. This allows for a visual, audible or tactile indication of probe position.

As previously noted, and/or discussed with respect to prior embodiments, assembly 592 generally includes urethral profiling apparatus 516 guidingly supported upon or by catheter 528 so ad to substantially extend through the lower urinary tract (i.e., from the external meatus 480 to at least the bladder neck 420). The catheter generally includes, as shown: a body 568, having proximal 570 and distal 572 ends; an anchor element 578 for secured positioning of the catheter at the bladder neck 420 in furtherance of receiving urine 410 from bladder 400; a valve manifold 580 opposite the anchor element 578 which includes a hub 584; and, a probe stop 590 intended to limit distal travel of the probe 526, shown positioned at the external urethral sphincter 460, relative to the catheter. As to quantification of the spatial relationships of and between the structures of the lower urinary tract, the dimension 593 associated with (i.e., between) the luer fitting 596 and the hub 584 is readily correlated to/with the dimension 591 associated with (i.e., between) the distal end 572 of the catheter and the probe 526.

It should be understood that the urethral profiling apparatus of the subject invention, in all its embodiments, are useful for characterization of the urethra, even for the purpose of understanding prostatic urethra compliance and volume displacements at a given pressure. This information is helpful in determining the physiology of the patients symptoms. Patients who may benefit from the use of these devices include select retention patients from all groups which include acute retention, chronic retention, episodic retention, pre-procedural retention, post minimally invasive benign retention, post minimally invasive oncology retention, post prostatic surgery retention, and post non-urethra related surgery retention patients. Finally, the embodiments of the subject invention described herein are also useful in the assessment of LUTS patients who, while not in retention, are nonetheless passing their urine with difficulty due to prostatic obstruction, sphincter dysnergia, or deficient bladder function.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. An endourethral assembly comprising a urethral profiling apparatus adapted so as to be supported by a catheter, and a probe wire having a proximal end and a distal end having a grip, said urethral profiling apparatus comprising a probe dimensioned so as to tactilely indicate constrictures of a urethral passageway, said probe supported at said proximal end of said probe wire for axial translation with respect thereto, at least a portion of said probe wire including spaced apart markings.

2. The assembly of claim 1 wherein at least a portion of said catheter includes at least a single marking.

3. The assembly of claim 2 wherein axial travel of said probe relative to said catheter is proximally limited by a portion of a proximal end of said catheter.

4. The assembly of claim 3 wherein said portion of said proximal end of said catheter comprises an anchor element.

5. The assembly of claim 4 wherein said anchor element comprises a reversibly expandable balloon.

6. The assembly of claim 3 wherein axial travel of said probe relative to said catheter is proximally limited by abutting engagement of a distal segment of said probe wire with a distal extremity of a distal portion of said catheter.

7. The assembly of claim 6 wherein said distal segment of said probe wire comprises said grip.

8. The assembly of claim 6 wherein said axial travel of said probe relative to said catheter is distally limited by abutting engagement of said probe with a stop of said catheter.

9. The assembly of claim 8 wherein said apparatus further includes a supplemental probe wire support, said supplemental probe wire support adapted to maintain said probe wire not greater than a preselected distance from said catheter.

10. The assembly of claim 9 wherein said supplemental probe wire support reversibly circumscribes said probe wire and said catheter.

11. The assembly of claim 9 wherein said supplemental probe wire support slidingly receives said probe wire for axial translation therethrough.

12. The assembly of claim 11 wherein said probe circumscribes an outer surface of said catheter.

13. The assembly of claim 12 wherein said stop defines a maximum cross section for a body of said catheter.

14. The assembly of claim 13 wherein said stop is positioned distally relative to said probe.

15. The assembly of claim 14 wherein said stop circumscribes said outer surface of said catheter.

16. The assembly of claim 15 wherein said stop is adapted to slidingly receive said probe wire.

17. The assembly of claim 13 wherein a radial projection from said body of said catheter defines said stop.

18. A urethral profile apparatus comprising an elongate member having proximal and distal ends, said proximal end comprising a tubular element and a probe integral thereto, said tubular element including a line of weakness in a wall thereof, said probe being adapted to be received upon a catheter for select positioning within a urethral passageway by axial translation of said elongate member via said distal end along a segment of the catheter, said probe being resiliently responsive and dimensioned so as to indicate constrictures of the urethral passageway.

19. A urethral profile apparatus comprising an elongate member having proximal and distal ends, said proximal end comprising a tubular element and a probe integral thereto, said tubular element including a slot in a wall thereof, said probe comprising a free end of said tubular element and adapted to be received upon a catheter for select positioning within a urethral passageway by axial translation of said elongate member via said distal end along a segment of the catheter, said probe being resiliently responsive and dimensioned so as to indicate constrictures of the urethral passageway.

* * * * *